(12) United States Patent
Farrar et al.

(10) Patent No.: US 9,861,488 B2
(45) Date of Patent: *Jan. 9, 2018

(54) KNEE JOINT PROSTHESIS

(71) Applicants: DePuy International, LTD., Leeds (GB); Chitranjan S. Ranawat, Alpine, NJ (US)

(72) Inventors: Richard Farrar, North Rigton (GB); Liam Rowley, West Yorkshire (GB); Andrew Cohen, Nr. Goole (GB); James Brooks, Ilkley (GB); Chitranjan S. Ranawat, Alpine, NJ (US)

(73) Assignees: DePuy International, Ltd., Leeds (GB); Chitranjan S. Ranawat, Alpine, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/173,856

(22) Filed: Jun. 6, 2016

(65) Prior Publication Data

US 2016/0278931 A1     Sep. 29, 2016

Related U.S. Application Data

(63) Continuation of application No. 13/945,986, filed on Jul. 19, 2013, now Pat. No. 9,358,118, which is a
(Continued)

(30) Foreign Application Priority Data

Feb. 8, 2003   (GB) .................................. 0302944.4
Nov. 17, 2003  (GB) .................................. 0326854.7

(51) Int. Cl.
*A61F 2/38*   (2006.01)
*A61F 2/30*   (2006.01)

(52) U.S. Cl.
CPC ............ *A61F 2/3886* (2013.01); *A61F 2/389* (2013.01); *A61F 2/3859* (2013.01);
(Continued)

(58) Field of Classification Search
CPC ........ A61F 2/38; A61F 2/3886; A61F 2/3859; A61F 2/3868
See application file for complete search history.

(56) References Cited

U.S. PATENT DOCUMENTS 4,209,861 A   7/1980  Walker et al.
4,298,992 A   11/1981 Burstein et al.
(Continued)

FOREIGN PATENT DOCUMENTS

EP   0 381 352 A1   8/1990
FR   2 758 456 A1   7/1998
(Continued)

OTHER PUBLICATIONS

International Search Report and Written Opinion for Application No. PCT/GB2004/000507, dated Jun. 2, 2004.
(Continued)

*Primary Examiner* — Jason-Dennis Stewart
(74) *Attorney, Agent, or Firm* — Nutter McClennen & Fish LLP

(57) ABSTRACT

A knee joint prosthesis which comprises a tibial component (4, 6) and a femoral component (2). The femoral component has condyles (14, 16) which act against the tibial component, directly or indirectly, during flexing of the knee. A cam (20) on the femoral component acts against a post (26) on the tibial component at high flex angles. The surface of the post which is contacted by the cam at high flex angles is convex when the post viewed generally perpendicular to the tibial bone contact and bearing surfaces, and the femoral bearing surface which is provided by the cam, where it
(Continued)

contacts the convex surface of the post at high flex angles, is locally concave (32) when viewed along the surface of the post which contacts the cam so that the area of contact between the post and the cam is greater at high flex angles than at lower flex angles.

18 Claims, 6 Drawing Sheets

Related U.S. Application Data continuation of application No. 10/566,147, filed as application No. PCT/GB2004/000507 on Feb. 9, 2004, now Pat. No. 8,500,817.

(52) U.S. Cl.
CPC ............... *A61F 2002/3082* (2013.01); *A61F 2002/30133* (2013.01); *A61F 2002/30332* (2013.01); *A61F 2002/30518* (2013.01); *A61F 2002/30688* (2013.01); *A61F 2002/30878* (2013.01); *A61F 2220/0025* (2013.01); *A61F 2220/0033* (2013.01); *A61F 2230/0015* (2013.01); *A61F 2310/00029* (2013.01)

(56) References Cited

U.S. PATENT DOCUMENTS

| | | |
|---|---|---|
| 4,634,444 A | 1/1987 | Noiles |
| 4,892,547 A | 1/1990 | Brown |
| 5,007,933 A | 4/1991 | Sidebotham et al. |
| 5,147,405 A | 9/1992 | Van Zile et al. |
| 5,370,699 A | 12/1994 | Hood et al. |
| 5,549,686 A | 8/1996 | Johnson et al. |
| 5,906,643 A | 5/1999 | Walker |
| 6,123,729 A | 9/2000 | Insall et al. |
| 6,325,828 B1 | 12/2001 | Dennis et al. |
| 8,500,817 B2 | 8/2013 | Farrar et al. |
| 9,358,118 B2 | 6/2016 | Farrar et al. |
| 2002/0010512 A1 | 1/2002 | Takei |
| 2003/0023314 A1 | 1/2003 | Burstein |
| 2009/0306785 A1 | 12/2009 | Farrar et al. |
| 2013/0310944 A1 | 11/2013 | Farrar et al. |

FOREIGN PATENT DOCUMENTS

| | | |
|---|---|---|
| JP | 10-513371 A | 12/1998 |
| JP | 11-313845 A | 11/1999 |
| JP | 2003-116892 A | 4/2003 |
| WO | 96/23460 A1 | 8/1996 |

OTHER PUBLICATIONS

UK Office Action for Application No. GB0302944.4, dated Aug. 13, 2003.
Japanese Office Action for Application No. 2006-502255, dated Apr. 21, 2009 (7 pages).

30°

60°

93°

125°

155°

KNEE JOINT PROSTHESIS

CROSS REFERENCE TO RELATED APPLICATIONS

The present application is a continuation of U.S. Ser. No. 13/945,986, filed Jul. 19, 2013, which is a continuation of U.S. Ser. No. 10/566,147, filed Aug. 4, 2009, now issued on Aug. 6, 2013, as U.S. Pat. No. 8,500,817, entitled "Knee Joint Prosthesis," which is a '371 application of PCT Application No. PCT/GB04/00507, filed Feb. 9, 2004, entitled "A Knee Joint Prosthesis," and which claims the priority of UK 0302944.4, filed Feb. 8, 2003 and UK 0326854.7, filed Nov. 17, 2003, all of which applications are hereby incorporated by reference in their entirety.

This invention relates to a knee joint prosthesis which comprises a tibial component and a femoral component.

Flexing of a knee joint involves a combination of rotation and translation of the femoral component relative to the tibial component. The femoral component of a whole knee joint prosthesis has a bearing surface provided by medial and lateral condyles. The surfaces of the condyles are convex. The condyles bearing surfaces act against the tibial component, directly or indirectly through a meniscal component. It is common for a knee joint prosthesis to include a meniscal component. This is frequently made from a material which permits low friction movement between the tibial and femoral components. For example, when the femoral component is formed from a metal such as a cobalt chromium based alloy, the bearing component can be formed from a polymer such as ultrahigh molecular weight polyethylene. The face of the meniscal component which faces towards the femoral component will generally have a pair of recesses in which the convex bearing surfaces of the condyles can articulate as the joint is flexed. In some knee joint prostheses, the tibial component will often have a planar bearing surface which faces towards the femur. A meniscal component will then have a planar lower surface which is also planar so that the meniscal component can slide relative to the tibial component as the joint is flexed. In other knee joint prostheses, the meniscal component can be allowed to rotate about the tibial axis but be fixed against translation. In yet other knee joint prostheses, the meniscal component can be fixed relative to the tibial component.

The stability of the joint through moderate flex angles is provided by the surface to surface contact between the curved surfaces of the condyles and the recesses in the meniscal component. Ligaments extending between the tibia and femur can control relative rotational and translational movement between the two bones. However, especially when it is anticipated that the joint will experience large flex angles, additional stability can be provided by a post which extends from the tibial component in a direction away from the tibia, and a cam on the femoral component which extends between the condyles at or towards their posterior ends. The cam can contact the post, at least at moderate to high flex angles, and thereby restrict translation of the femoral component relative to the tibial component. The post can be provided on a bearing component of the knee. The material of the bearing component is often selected for its low coefficient of friction when in contact with the metallic bearing surface of the femoral or tibial component. The properties of the selected material might not always be optimised for bearing the load which is applied by the cam at high flex angles.

While contact between a post on the tibial component and a cam on a femoral component is intended to restrict translation of the femoral component relative to the tibial component, it will generally be desired that it should not restrict relative rotation between the femoral and tibial components. Accordingly, the area of contact between the cam and the post will be kept to a minimum, especially as close as possible to point contact. This can be achieved by arranging both the post and the cam to have rod or bar-like shapes, which are convex at the points where they are in contact when viewed along their lengths, and for them to intersect roughly perpendicular to one another.

The present invention provides a knee joint prosthesis in which the femoral bearing surface is provided in part by a cam which extends between the condyles, which is concave where it contacts a post on the tibial component at high flex angles.

Accordingly, in one aspect, the invention provides a knee joint prosthesis which comprises:

a. a tibial component which has a bone contact surface for contacting a patient's resected tibia, and an opposite bearing surface, and a post extending from the bearing surface in a direction generally away from the bone contact surface, and b. a femoral component which has a bearing surface provided by medial and lateral condyles, and by a cam which is located between the condyles at or towards their, posterior ends, in which the condyles of the femoral bearing surface act against the bearing surface of the tibial component, directly or indirectly, during flexing of the knee and the cam on the femoral component acts against the post on the tibial component at high flex angles, and in which:

a. the surface of the post which is contacted by the cam at high flex angles is convex when the post viewed generally perpendicular to the tibial bone contact and bearing surfaces, and b. the femoral bearing surface which is provided by the cam, where it contacts the convex surface of the post at high flex angles, is locally concave when viewed along the surface of the post which contacts the cam so that the area of contact between the post and the cam is greater at high flex angles than at lower flex angles.

The knee joint prosthesis of the present invention has been found to give rise to the advantage that the ability of the post to bear the loads imposed on it by the cam at high flex angles is enhanced. This has been found to arise from the larger area of contact between the cam and the post at high flex angles than is available with prostheses in which the surface of the cam is not concave where it contacts the post. The larger area of contact contributes to greater stability of the joint prosthesis at high flex angles, for example above 120°, especially above 130°, or above 150°. The provision of a localised concave region of the cam means that, at lower flex angles, the flexibility of the cam is preserved by virtue of the fact that the contact angle between the cam and the post is not increased.

Preferably, the ratio of the contact area between the post and the cam at a flex angle of 150° to the said contact area when the flex angle is 90° is at least about 2.0, preferably at least about 2.5. Preferably, the ratio of the contact area between the post and the cam at a flex angle of 145° to the said contact area when the flex angle is 90° is at least about 1.3, preferably at least about 1.4.

The increased area of contact between the cam and the post can mean that the joint is more stable, and less prone to dislocation, than is the case in which the contact between a cam and post is restricted to point contact.

The cam can be generally bar-like having a generally rounded cross-section when viewed along its length, at least around those parts of its periphery at which it contacts the post on the tibial component. The cam can be connected to the condyles at its opposite ends. It can also be connected to other parts of the femoral component at other points along its length, and possibly along its entire length.

The cam will appear to be concave when viewed sagittal (from one side) and transversely (along the femoral axis) in the region in which it is intended to contact the post at high flex angles, and convex around the other parts of the periphery at which it contacts the post at other flex angles. Preferably, the radius of curvature of the cam in the centre of the concave region, when viewed from one side, is at least about 25 mm, more preferably at least about 30 mm, especially at least about 37 mm. Preferably, the said radius of curvature is not more than about 60 mm, more preferably not more than about 50 mm, especially not more than about 43 mm. In a preferred embodiment, the radius of curvature of the cam in the centre of the concave region, when viewed from one side, is about 40 mm.

Accordingly, it can be preferred for the said round cross-section of the cam to be interrupted in the region where the cam contacts the convex surface of the post at high flex angles so that, in that region, the cross-section is flattened or concave. Accordingly, it can be preferred that the cross-section of the cam is rounded at and towards its ends, and flattened or concave in a central region between its ends where it contacts the convex surface of the post at high flex angles.

Preferably, the depth of the concave portion of the cam, measured relative to the surface of the cam at each side of the concave portion, is at least about 0.5 mm. Preferably, the said depth is not more than 1.2 mm, more preferably not more than about 1.0 mm.

The transition between the convex surface of the cam and the concave surface in the region in which it will contact the post at high flex angles should be carefully shaped so that the area of contact between the cam and the post does not decrease significantly as the angle of flex increases to bring the concave region of the cam into contact with the post. This can be achieved by making the edge of the concave region rounded. The radius of curvature of the concave region rounded edge can vary around the concave region. The radius of curvature can be greatest at the posterior edge. For example, the radius of curvature at the at the anterior edge of the concave region is preferably at least about 1.0 mm, more preferably at least about 1.5 mm, especially at least about 1.75 mm, for example about 2.0 mm. The radius of curvature at the anterior edge is preferably not more than about 3.0 mm, more preferably not more than about 2.5 mm. The radius of curvature at the posterior edge of the concave region is preferably not more than about 6.0 mm, more preferably not more than about 5.0 mm, for example not more than about 4.75 mm. The radius of curvature at the posterior edge is preferably at least about 3.0 mm, more preferably at least about 4.0 mm.

Preferably, the bearing surface on the cam is configured so that the surface is concave where it contacts the post when the flex angle between the femur and the tibia is at least about 130°, more preferably at least about 120°. The bearing surface on the cam will preferably then be concave where it contacts the post at all flex angles greater than about 120°, preferably at all angles greater than about 130°, for example at all angles up to about 150°, preferably at all angles up to about 155°. Preferably, the area of contact between the bearing surfaces of the cam and the post increases as the flex angle increases from an angle of not less than about 115°, preferably not less than about 120°, so that the area of contact reaches a maximum when the flex angle is not less than about 145°, preferably not less than about 150°. The area of contact will increase from a shape which approximates to a point, to a shape which is generally rounded, especially oval. As the area of contact increases through the increasing flex angle, the size of the oval area of contact increases.

The flex angle at which the concave portion of the cam bearing surface engages the post is determined by the orientation angle of the cam. The orientation angle is the angle between the sagittal plane and a line extending normally through the centre of the concave portion. Preferably, the orientation angle is at least about 15°, more preferably at least about 20°. Preferably, the orientation angle is not more than about 30°, more preferably not more than about 25°. Preferably, the orientation angle is about 22°. When the flex angle is about 22°, contact between the post concave portion of the cam can occur at flex angles greater than about 120°, with contact area at a flex angle of about 155°.

When the cam is bar-like and extends between the condyles, it can be preferred for the area of the cam at which it engages the post to increase so that, when the area is at its maximum, it extends to a point which is not more than 1.5 mm from the ends of the bar where it joins the condyles, preferably not more than 1.0 mm.

The tibial component can comprise an implant part and a bearing part. The implant part and the bearing part can be made from different materials. For example, the implant part can be made from a metal such as a cobalt chromium alloy or a titanium based alloy. The bearing part can be made from a polymer such as an ultrahigh molecular weight polyethylene (UHMWPE). The bearing part will often be fixed to the implant part so that it does not move relative to it during articulation of the knee. For example, the bearing part can fit into a recess which is defined by an upstanding wall, extending around at least part of the periphery of the tibial part. Alternatively (or in addition), the implant part and the bearing part can fit together by an arrangement which comprises at least one interdicting boss and recess. It will generally be preferred that the bearing part is fixed against translation relative to the implant part, but can rotate relative to it. This can be achieved by means of a peg on the bearing part which is received in an axially expending bore in the implant part. For example, the implant part can include a hollow peg which can be received in an appropriately shaped cavity in the resected tibia. The space within the peg on the implant part can receive a peg on the bearing part. Preferably the pegs on the two parts, and the recess within the peg on the implant part, are conical with a circular cross-section.

A knee joint prosthesis in which the tibial component comprises implant and bearing parts, in which the bearing part is fixed against translation relative to the implant part, is sold under the trade mark SIGMA by DePuy Orthopaedics Inc of Warsaw, Ind., USA.

The post can be provided on the bearing part of an tibial component which comprises separate implant and bearing parts. A bearing part which includes a post will generally be formed as a single piece which consists of the same material throughout (for example a polymeric material such as UHMWPE).

The height of the post will be selected to ensure that the cam will not ride over the top of the post at high flex angles. The width and depth of the post (measured parallel to the sagittal plane) should be sufficient to ensure that the post can withstand loads imposed on it by the cam when the knee joint is flexed. The appropriate selection of these design features is known, for example as in the knee joint prostheses sold by Orthomet Inc under the trade mark AXIOM, and by Smith & Nephew Richards under the trade mark GENESIS (Posterior Stabilised).

Preferably, the surface of the post which is contacted by the cam at high flex angles is convex when viewed from above (viewed generally along the tibial axis). Preferably, the surface of the post which is contacted by the cam is flat, or possibly concave, when viewed sagittally (from one side).

It has been found that, by appropriate shaping of the cam and the post, the area of contact between the two can be at least about 50 mm$^2$, preferably at least about 75 mm$^2$, for example from 80 mm$^2$ and up to 120 mm$^2$ or more, at high flex angles (for example 140° or 145° or 150°). This is very much greater than can be achieved with knee prosthesis designs in which the surface of the cam is convex. As a result, the post is better able to bear the loads imposed on it by the cam at high flex angles. Furthermore, the increased area of contact between the cam and the post can mean that the joint is more stable, and less prone to dislocation, than is the case in which the contact between a cam and post is restricted to point contact. Preferably, the area of contact between the cam and the post at lower flex angles can be not more than about 25 mm$^2$, more preferably not more than about 15 mm$^2$, for example not more than about 12 mm$^2$, or not more than about 8 mm$^2$.

Embodiments of the invention will now be described by way of example with reference to the accompanying drawings, in which.

Figure 1:
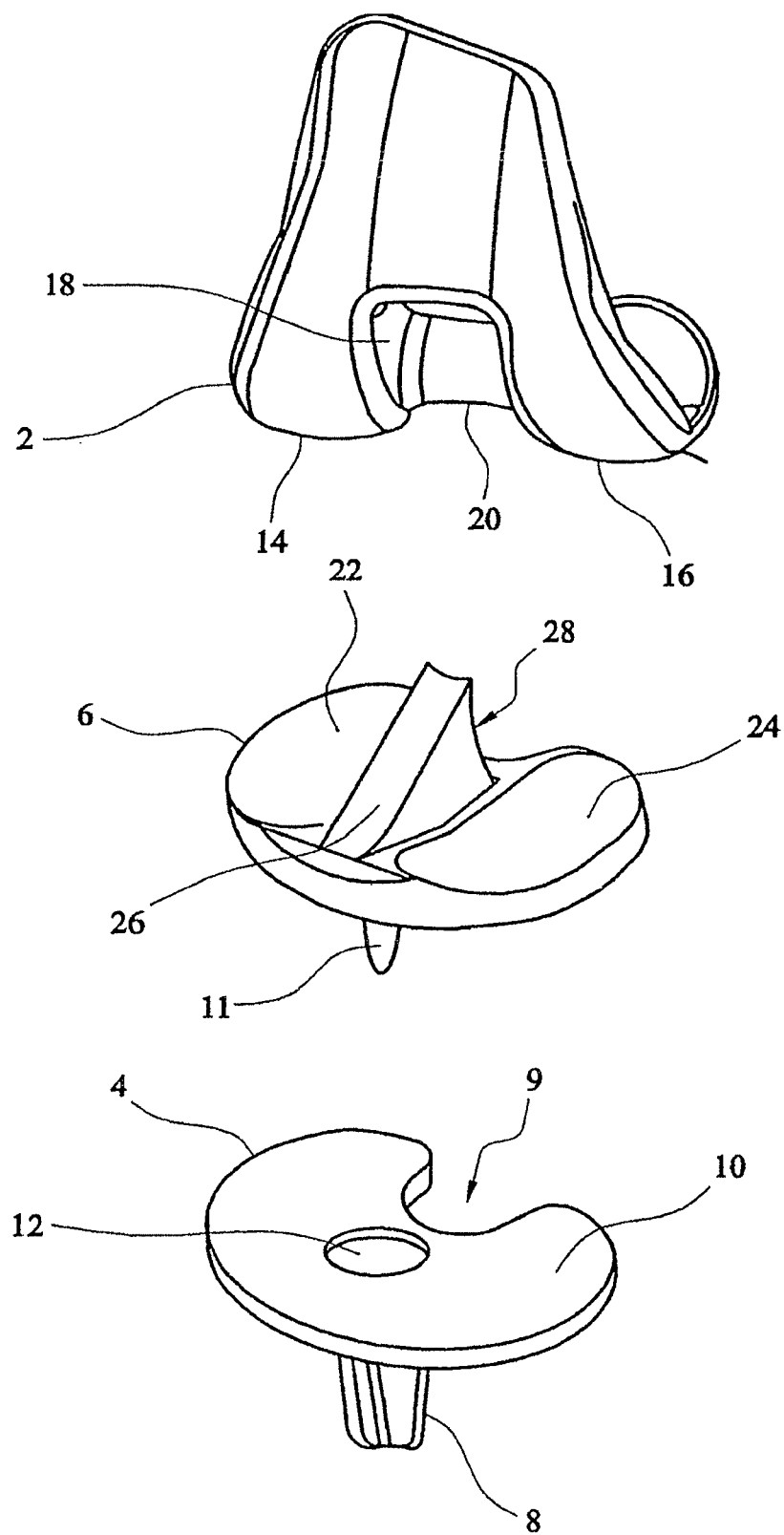
FIG. 1 is an exploded view of a knee prosthesis according to the present invention.

Referring to the drawings, FIG. 1 shows a knee joint prosthesis which comprises a femoral component 2 and a tibial component. The tibial component comprises an implant part 4 and a bearing part 6. The femoral component and the implant part of the tibial component are formed from a cobalt chromium based alloy. The implant part of the tibial component has a downwardly extending peg 8 which can be received in an appropriately shaped cavity in the resected tibia. The upward surface 10 is generally planar. It has a central opening 12 which communicates with a conical bore within the downwardly extending peg 8. A notch 9 is formed in the implant part of the tibial component to accommodate ligament tissue.

The femoral component has medial and lateral condyles 14, 16, each of which has a bearing surface with appropriately smooth finish. There is a recess 18 between the condyles. The recess is defined posteriorly by a bar 20 which extends between the condyles. The bar is generally rounded in cross-section when viewed from one side along the medial-lateral axis. It has a finished bearing surface around at least part of its curved surface, at least in a central region which provides a cam.

The bearing part 6 of the tibial component is made from a polymeric material such as ultrahigh molecular weight polyethylene. Its lower surface is planar and has a conical peg depending from it. The peg is sized so that it fit snugly within the conical bore 12 in the implant part of the tibial component. The peg and the bore have a circular cross-section so that the bearing part can rotate relative to the implant part.

The upper surface of the bearing part has two concave recesses 22, 24 formed in it in which the condyles 14, 16 can be received, and can slide during articulation of the joint. A post 26 extends upwardly from the bearing part. The post has a bearing surface 28 on its posteriorly facing edge. When viewed from above along the tibial axis, the posteriorly facing surface of the post is convex. When viewed from the side, the posteriorly facing surface of the post is straight, or slightly concave.

Figure 2:
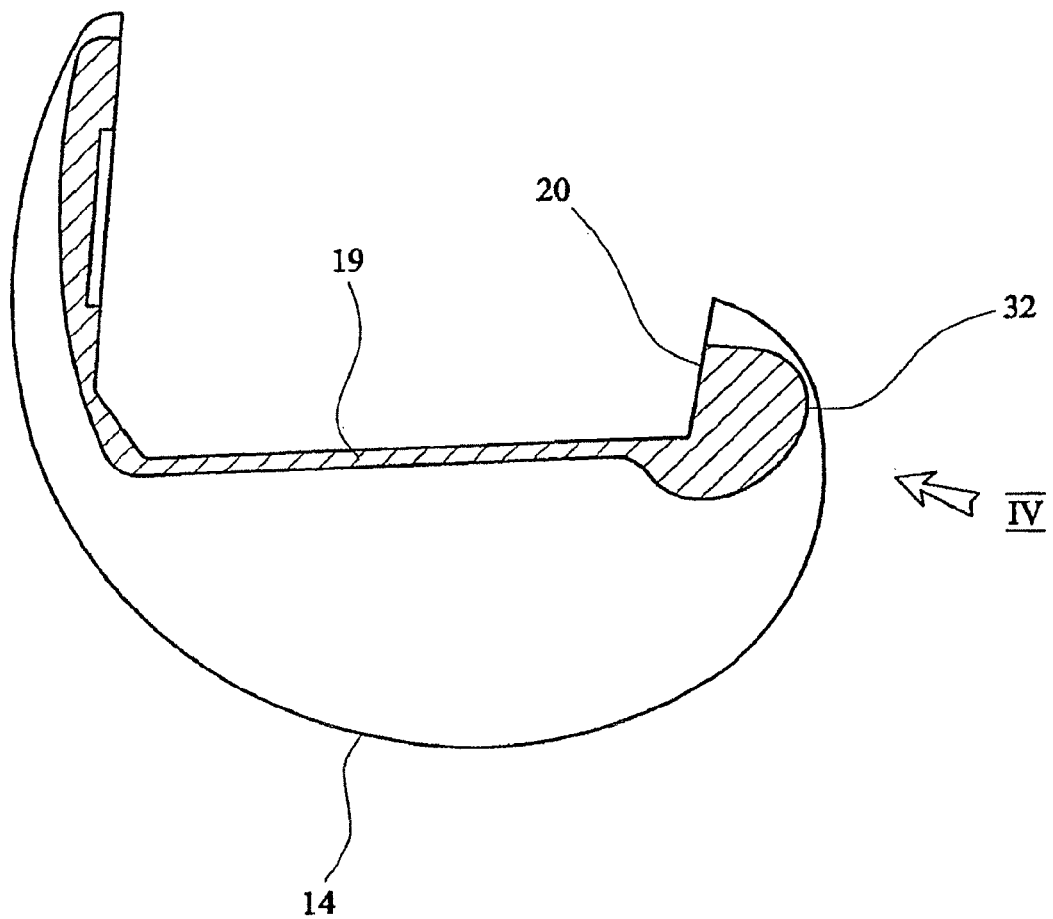
FIG. 2 is a sectional elevation through the femoral component shown in FIG. 1, on the line II-II.

One of the condyles 14 of the femoral component 2 is visible in FIG. 2. Also visible is the bar 20. The bar can be seen to have a generally rounded shape when viewed from the side. The bar is formed integrally with a web 19 which extends between the condyles, defining a recess between the condyles into which the post extends during flexing of the joint.

Figure 3:
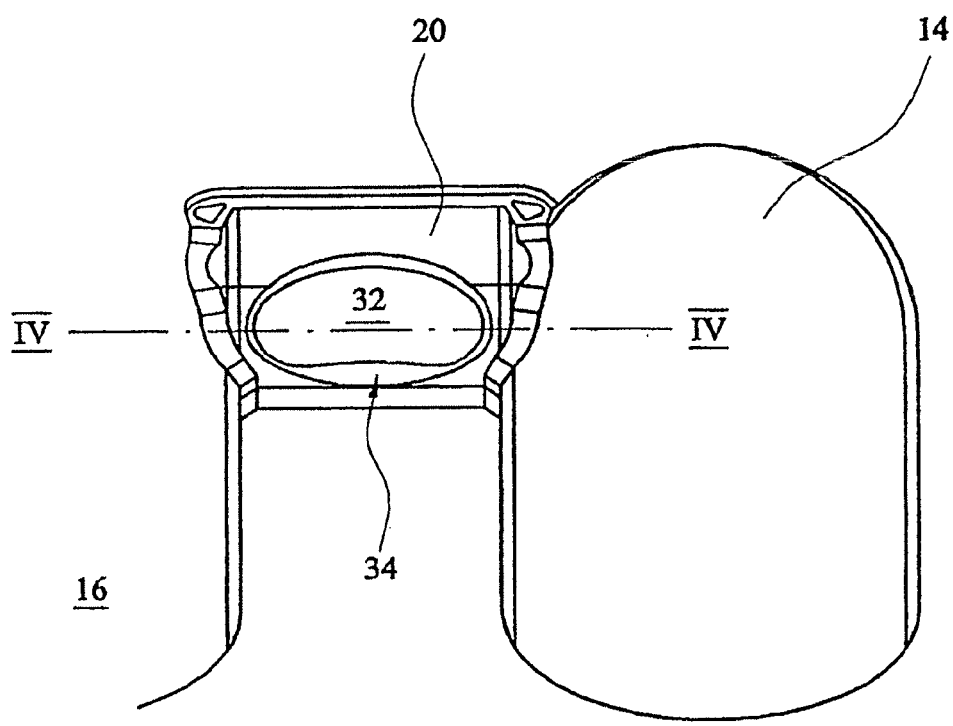
FIG. 3 is an enlarged view showing the portion of the cam on the femoral component in which the bearing surface is concave along the direction marked by the arrow IV
Figure 4:
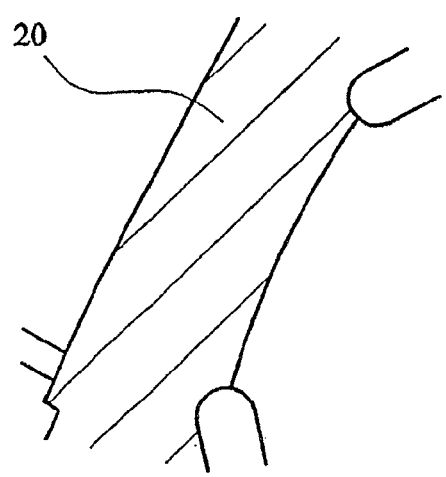
FIG. 4 is a partial cross-section through the cam on the femoral component on the line IV-IV.

The concave portion 32 of the bar is shown in more detail in FIGS. 3 and 4. As shown in FIG. 3, the concave portion 32 has rounded transitions at its edge. The radius of curvature at the rounded transition at the posterior edge is greater than at the other edges. The radius at the posterior edge 34 is about 4.6 mm, and the radii at the anterior, medial and lateral edges is about 2.0 mm. The concave portion extends to within about 1.5 mm of the condyles at each end of the bar 20.

As shown in FIG. 4, the concave portion of the bar is rounded when it is viewed in a direction which is parallel to the bearing surface of the post (when the concave portion and the post are aligned in contact with one another at maximum flexing of the joint). The radius of curvature is about 40 mm. This is little more than the radius of curvature of the post (when viewed from above along the tibial axis) with which it is in contact at high flex angles. When the concave portion of the bar is viewed from one side (as in FIG. 2), it is approximately straight.

The bar is polished on that part of its surface which is intended to contact the post during articulation of the knee. There is a concave portion 32 in that part of the bar which contacts the post at high flex angles.

Figure 5A:
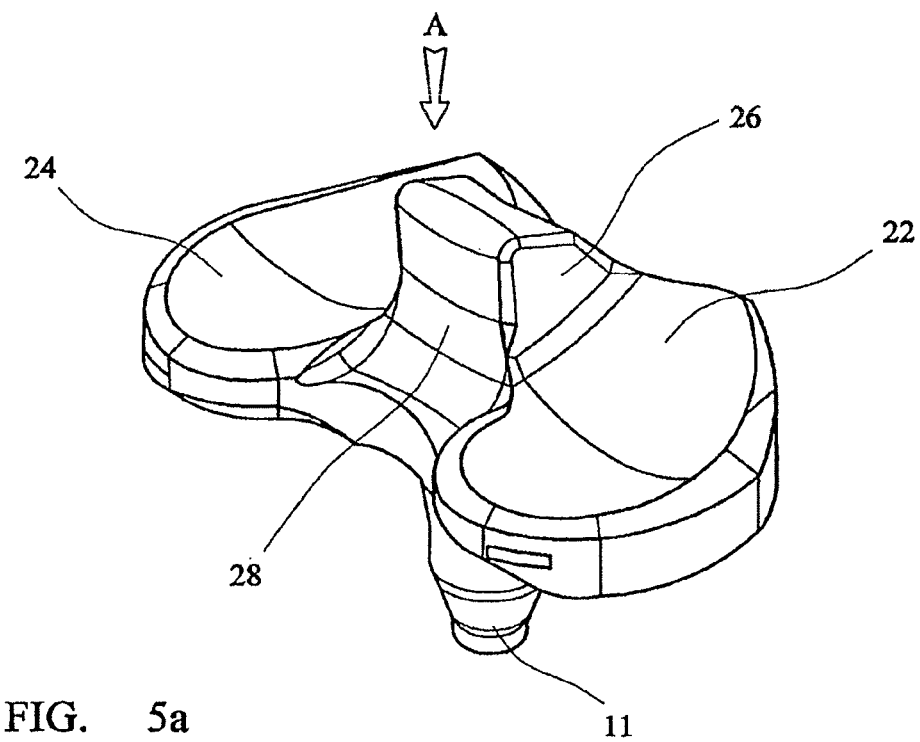
FIGS. 5a and 5b are isometric and side elevation views of the bearing component shown in FIG. 1.
Figure 5B:
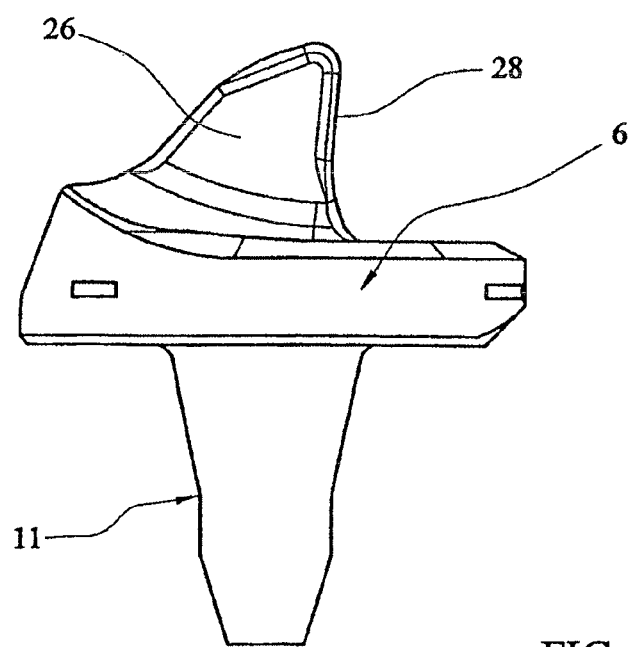

FIGS. 5a and 5b show the bearing part 6 of the tibial component. The bearing surface 28 of the post 26 is essentially planar towards its upper end (as shown in FIG. 5b). The bearing surface is also essentially planar along the medial-lateral axis, that is when viewed from above (along the line defined by the arrow "A").

Figure 6A:
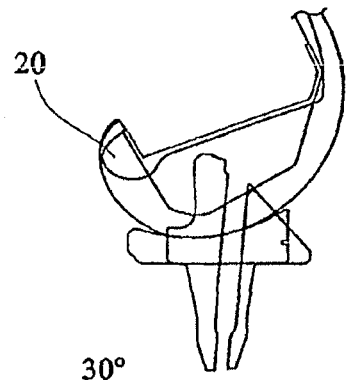
FIGS. 6a to 6e are views from one side showing how the femoral component of a knee joint prosthesis of the kind shown in FIG. 1 articulates against the tibial component.

As shown in FIG. 6a, at moderate flex angles (up to about 90°), contact between the femoral and tibial components is restricted to contact between the condylar bearing surfaces 14, 16 of the femoral component which engage the recesses 22, 24 in the bearing part of the tibial component. During flexing of the joint through moderate flex angles, the femoral component can rotate and translate relative to the tibial component. At a flex angle of about 90°, the cam provided by the bar 20 engages the post 26 on the bearing component. The action of the post against the cam can control further translational movement of the femoral component relative to the tibial component, in the plane thereof, so that continued flexing of the knee is restricted largely to a pivoting motion, as shown in sequence in FIGS. 6b to 6d.

Figure 6B:
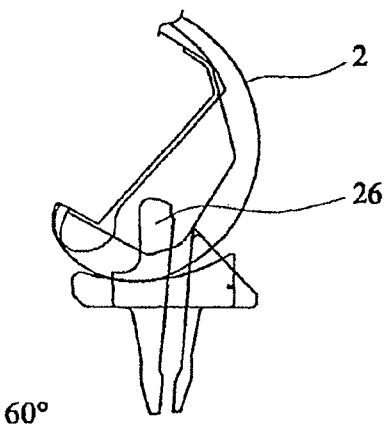
Figure 6C:
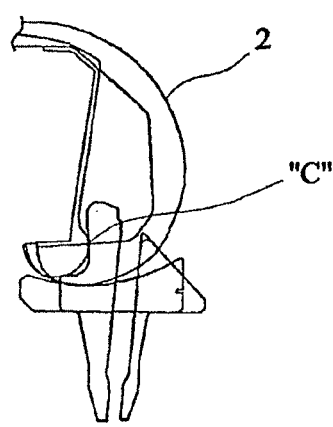
Figure 6D:
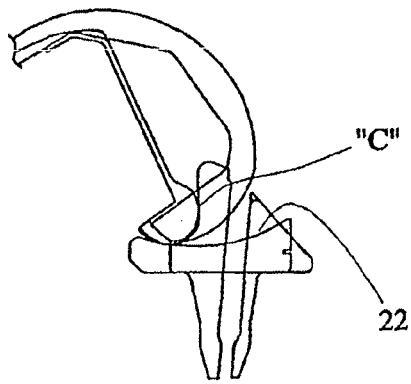
Figure 6E:
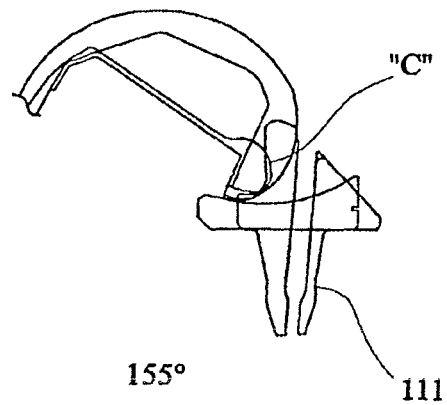

As shown in FIG. 6b, at a flex angle of about 90°, the curved bearing surface on the bar 20 engages the bearing surface on the post 26, the point marked "C". At moderate flex angles (up to 115 or 125°), the bearing surface on the bar is convex where it contacts the post. The area of contact between the bar and the post is therefore restricted to a small area. This will be point contact (in the absence of any localised deformation of the components) when the each of the relevant bearing surfaces is convex at the point of contact. Continued flexing of the knee joint beyond 125° results in rotation and sliding of the femoral component relative to the tibial component, about an axis which is approximately fixed. As the flex angle increases, the shear forces applied to the post by the bar, parallel to the plane of the resected tibia, increase.

Figure 7:
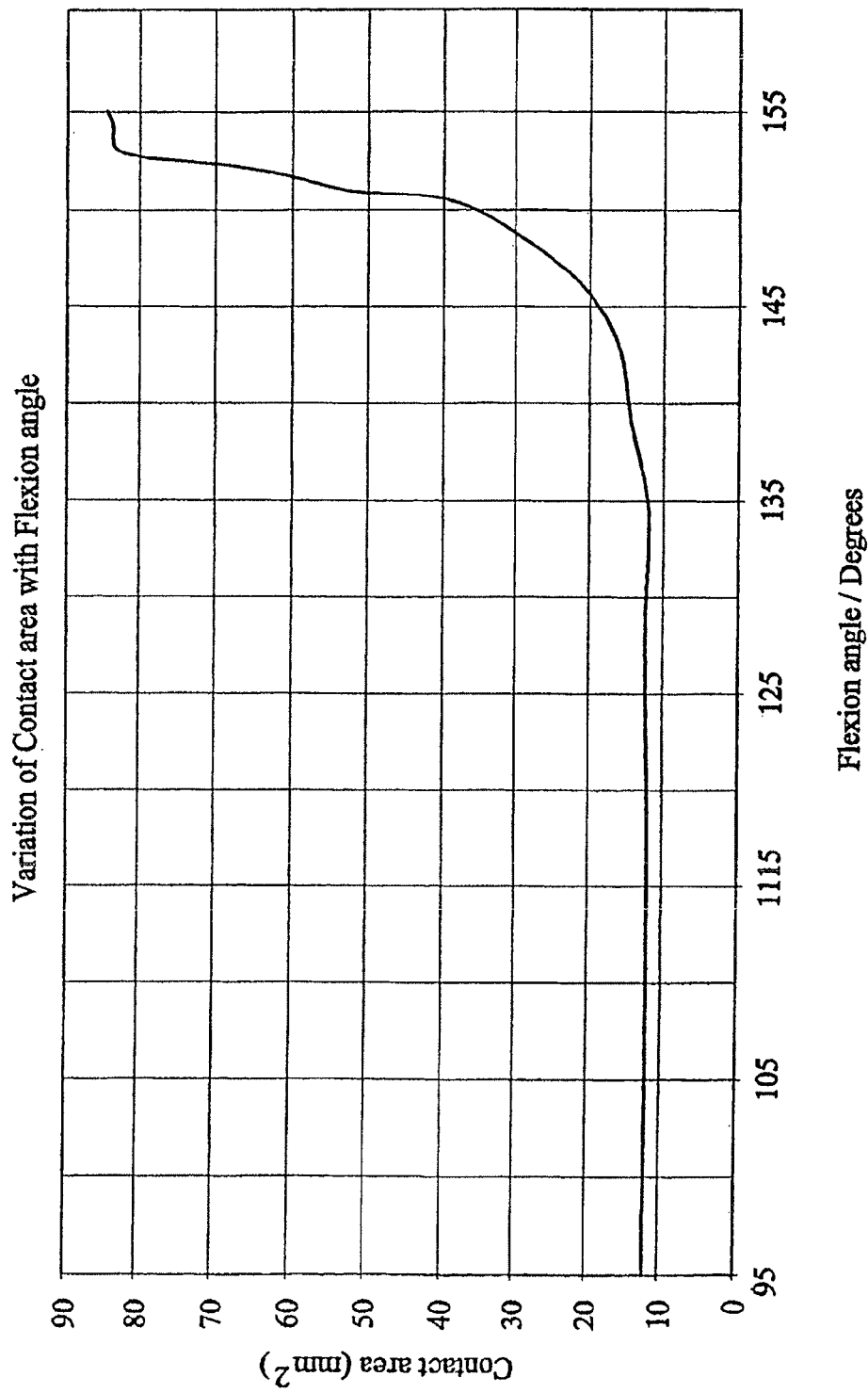
FIG. 7 is a graph which depicts the variation in contact area between the femoral and tibial components of a knee joint prosthesis with changes in the angle of articulation of the joint.

Also as the flex angle increases and the bar 20 rotates relative to the post 26, the concave portion 32 of the bar moves rotationally towards the post. The area of contact between the concave portion and the post increases during continued rotation of the femoral component relative to the tibial component until the area of contact reaches a maximum at a flex angle of around 150 to 155°. The variation in the area of contact with angle of articulation is shown roughly in FIG. 7.

The invention claimed is:

1. A knee joint prosthesis which comprises:
   a. a tibial component which has a bone contact surface for contacting a patient's resected tibia, and an opposite bearing surface, and a post extending from the bearing surface in a direction generally away from the bone contact surface, and
   b. a femoral component which has a bearing surface provided by medial and lateral condyles, and by a cam which is located between the condyles at or towards their posterior ends, in which the condyles of the femoral bearing surface act against the bearing surface of the tibial component during flexing of the knee and when the knee is flexed through a predetermined flex angle, wherein flex angles greater than the predetermined flex angle are high flex angles and flex angles less than the predetermined flex angle are lower flex angles, the cam on the femoral component acts against the post on the tibial component at high flex angles, and in which:
   a. the surface of the post which is contacted by the cam at high flex angles is convex when the post viewed generally perpendicular to the tibial bone contact and bearing surfaces, and
   b. the femoral bearing surface which is provided by the cam, where it contacts the convex surface of the post at high flex angles, is locally concave when viewed along the surface of the post which contacts the cam so that the area of contact between the post and the cam is greater at high flex angles than at lower flex angles.

2. A knee joint prosthesis as claimed in claim 1, in which the ratio of the contact area between the post and the cam at a flex angle of 150° to the said contact area when the flex angle is 90° is at least about 2.0, preferably at least about 2.5.

3. A knee joint prosthesis as claimed in claim 2, in which the said round cross-section of the cam is interrupted in that region where the cam contacts the convex surface of the post at high flex angles so that, in that region, the cross-section is flattened or concave.

4. A knee joint prosthesis as claimed in claim 2, in which the cam is formed integrally with a web which extends between the condyles, in contact with the cam at a point where the cam does not contact the post during articulation of the joint.

5. A knee joint prosthesis as claimed in claim 2, in which when the maximum area of the cam which contacts the post extends to a point which is not more than 1.5 mm from the ends of the cam where it joins the condyles.

6. A knee joint prosthesis as claimed in claim 1, in which the cam is generally bar-like having a generally round cross-section when viewed along its length.

7. A knee joint prosthesis as claimed in claim 6, in which the cross-section of the cam is rounded at and towards its ends, and flattened or concave in a central region between its ends where it contacts the convex surface of the post at high flex angles.

8. A knee joint prosthesis as claimed in claim 1, in which the bearing surface on the cam is configured so that the surface its concavity is greater in the region where it acts against the post when the flex angle between the femur and the tibia is at least about 130° than in the region where it acts against the post at smaller flex angles.

9. A knee joint prosthesis as claimed in claim 1, in which the tibial component comprises a tibial implant part for implantation in the tibia, and a bearing part, which can be positioned between the tibial implant part and the femoral component.

10. A knee joint prosthesis as claimed in claim 1, in which the depth of the concave portion of the cam, measured relative to the surface of the cam at each side of the concave portion, is at least about 0.5 mm.

11. A knee joint prosthesis as claimed in claim 1, in which the depth of the concave portion of the cam, measured relative to the surface of the cam at each side of the concave portion, is not more than 1.2 mm.

12. A knee joint prosthesis as claimed in claim 1, in which the radius of curvature at the anterior edge of the concave region is at least about 1.0 mm.

13. A knee joint prosthesis as claimed in claim 1, in which the radius of curvature at the at the anterior edge of the concave region is not more than about 3.0 mm.

14. A knee joint prosthesis as claimed in claim 1, in which the radius of curvature at the anterior edge is not more than about 6.0 mm.

15. A knee joint prosthesis as claimed in claim 1, in which the radius of curvature at the anterior edge is at least about 3.0 mm.

16. A knee joint prosthesis as claimed in claim 1, wherein the predetermined flex angle is not less than about 115 degrees.

17. A knee joint prosthesis as claimed in claim 1, wherein the predetermined flex angle is at least about 120 degrees.

18. A knee joint prosthesis as claimed in claim 1, wherein the predetermined flex angle is at least about 130 degrees.

* * * * *